United States Patent [19]

Saruyama et al.

[11] Patent Number: 5,057,476

[45] Date of Patent: Oct. 15, 1991

[54] PLATINUM CATALYST COMPOSITION, METHOD FOR ITS PREPARATION AND CURABLE ORGANOPOLYSILOXANE COMPOSITIONS CONTAINING SAME

[75] Inventors: Toshio Saruyama, Sakura; Hideko Takeda, Funabashi; Atshushi Togashi, Ichihara, all of Japan

[73] Assignee: Dow Corning Toray Silicone Company, Ltd., Tokyo, Japan

[21] Appl. No.: 570,669

[22] Filed: Aug. 22, 1990

[30] Foreign Application Priority Data

Aug. 31, 1989 [JP] Japan ................................. 1-225230

[51] Int. Cl.$^5$ ............................................. B01J 31/28
[52] U.S. Cl. .................................. 502/158; 502/152; 502/169
[58] Field of Search ........................ 502/152, 158, 169

[56] References Cited

U.S. PATENT DOCUMENTS 3,419,593 12/1968 Willing ............................. 260/448.2
3,715,334 2/1973 Karstedt ............................. 260/46.5
3,775,452 11/1973 Karstedt ............................. 260/429
4,288,345 9/1981 Ashby ................................. 252/431

*Primary Examiner*—Patrick P. Garvin
*Assistant Examiner*—Brent M. Peebles
*Attorney, Agent, or Firm*—George A. Grindahl

[57] ABSTRACT

A platinum catalyst composition having improved thermal stability, and all of the utilities of platinum catalyst compositions of trhe art, is provided by mixing certain organosiloxanes which contain aryl and alkenyl groups, such as 1,3-divinyl-1,3-diphenyldimethyldisiloxane, in a quantity of at least 2 moles, with a platinum complex having as a ligand an organosiloxane which contains alkyl and alkenyl groups, such as 1,3-divinyltetramethyldisiloxane (or a mixture of said platinum complex and said organosiloxane), in a quantity of 1 mole of platinum atoms. In a preferred embodiment the mixture is distilled in vacuo to remove part or all of the organosiloxane which contains alkyl and alkenyl groups, and most preferably to remove at least a portion of the complexed organosiloxane which contains alkyl and alkenyl groups.

15 Claims, No Drawings

PLATINUM CATALYST COMPOSITION, METHOD FOR ITS PREPARATION AND CURABLE ORGANOPOLYSILOXANE COMPOSITIONS CONTAINING SAME

BACKGROUND OF THE INVENTION

The present invention relates to a platinum catalyst composition which may be used as a catalyst, inter alia, of the hydrosilylation reaction, to a method for its preparation, and to a curable organopolysiloxane composition which contains said platinum catalyst composition.

A large number of platinum compounds are known as hydrosilylation reaction catalysts. Among these, the platinum/alkenylsiloxane complex catalyst compositions as disclosed in Japanese Patent Publication Number 42-22924 (22,924/67) and Japanese Patent Publication Number 46-28795 (28,795/71) have a high catalytic activity and are useful as hydrosilylation reaction catalysts. These are prepared by a reaction, for example, between alkenyl group-containing siloxane and chloroplatinic acid.

However, this type of platinum catalyst composition generally suffers from a poor storage stability, and, unless careful attention is paid to its method of storage, it readily deteriorates into platinum black with a concomitant substantial loss in catalytic activity. For example, the catalyst suffers from a loss in activity within a few hours merely upon an increase in storage temperature. Moreover, its storage stability is also sharply reduced by other substances which may be compounded into the reaction system.

A large number of methods have been introduced in order to solve these problems. For example, Japanese Patent Publication Number 47-23679 (23,679/72) proposes that the storage stability be increased by removing the halide in the prepared platinum/alkenylsiloxane complex catalyst composition. In this method, the platinum/alkenylsiloxane complex catalyst composition is stored as such or in a neutral medium such as polysiloxane, and this represents an effective approach as long as the catalyst composition is placed in an environment free of temperature increases. However, this method is unsatisfactory with regard to the storage stability in the presence of non-neutral substances or in an environment suffering from temperature increases.

Japanese Patent Publication Numbers 46-28795 (28,795/71) and 46-29731 (29,731/71) disclose a platinum/alkenylsiloxane complex catalyst composition which is prepared using phenyl group-containing alkenylsiloxane. However, one encounters very low platinum-based yields in the preparation by conventional methods of platinum complex catalyst compositions having these phenyl-containing alkenylsiloxane ligands, and the problem then arises of poor economics.

In addition, Japanese Patent Application Laid Open (Kokai) Number 56-136655 (136,655/81) proposes a method for the preparation of a platinum/alkenylsiloxane complex catalyst composition via the bis-(1,5-cyclooctadiene)/Pt complex by ligand exchange with siloxane which contains the alkyl and alkenyl groups. Again, the economics of this method are poor due to the low yield of the intermediate bis-(1,5-cyclooctadiene)/Ft complex and due to the reduction in yield arising from the rapid decomposition to platinum black when this intermediate's solution comes into contact with the air.

Thus, as discussed above, there have already been various attempts at improving the storage stability of Pt/alkenylsiloxane complex catalyst compositions. Nevertheless, aside from storage in a neutral medium in a low temperature ambient, no Pt/alkenylsiloxane complex catalyst composition has been discovered which evidences an excellent storage stability as well as good economics, nor has a method for the preparation of same been discovered.

BRIEF SUMMARY OF THE INVENTION

The present inventors achieved the present invention as the result of extensive investigations directed at solving the aforementioned problems.

A platinum catalyst composition having improved thermal stability is provided by mixing certain organosiloxanes which contain aryl and alkenyl groups, in a quantity of at least 2 moles, with a platinum complex having as a ligand an organosiloxane which contains alkyl and alkenyl groups, or a mixture of said platinum complex and said organosiloxane, in a quantity of 1 mole of platinum atoms.

DETAILED DESCRIPTION OF THE INVENTION

The present invention relates to a platinum catalyst composition composed of (A) a platinum complex having as a ligand an organosiloxane which has no more than 8 silicon atoms in each molecule and contains alkyl and alkenyl groups and which has in each molecule at least one bond as represented by the following formula

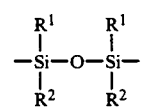

wherein $R^1$ is an alkyl group having no more than 6 carbon atoms and $R^2$ is an alkenyl group, or a mixture of said platinum complex and said organosiloxane; and (B) an organosiloxane which contains aryl and alkenyl groups and has no more than 8 silicon atoms in each molecule and which contains in each molecule at least one bond as represented by the following formula

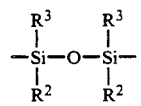

wherein $R^3$ is an aryl group and $R_2$ is defined as above, in a quantity of at least 2 moles of component (B) per 1 mole platinum atoms in component (A).

To explain this in greater detail, component (A) comprises a platinum complex having as ligand an organosiloxane which has no more than 8 silicon atoms in each molecule and contains alkyl and alkenyl groups and which has in each molecule at least one bond as represented by the following formula.

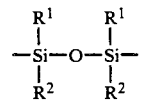

In the preceding formula $R^1$ is an alkyl group having no more than 6 carbon atoms such as methyl, ethyl, propyl, etc., and $R^2$ is an alkenyl group such as vinyl, allyl, etc.

Component (A) can also be the mixture of said platinum complex and said organosiloxane.

This component (A) may consist simply of the aforementioned platinum complex, but it may also be a mixture of said platinum complex with organosiloxane identical to or of the same type as the (alkyl+alkenyl)-containing organosiloxane coordinated in said platinum complex. (Alkyl +alkenyl)-containing organosiloxane not coordinated within the platinum complex should be present as a general matter at no more than 30 moles per 1 mole platinum atoms in the platinum complex.

This component (A) is in fact known, for example, as disclosed in Japanese Patent Publication Number 42-22924. In general, it is prepared by reacting, with heating, (alkyl+alkenyl)-containing siloxane with haloplatinic acid or haloplatinic acid salt. In the preparation of component (A) by this method, the alkenyl group in the starting (alkyl+alkenyl)-containing siloxane is generally the vinyl group. Moreover, it is preferred that the alkyl group be the methyl group considering the economics and prevention of side reactions during preparation of the platinum complex comprising component (A). Although no specific restriction is placed on groups which may be present in addition to the alkenyl and alkyl groups, it is necessary in particular to avoid aryl groups since this causes a reduction in the platinum yield in the preparation of component (A). Examples of this (alkyl+alkenyl)-containing siloxane are 1,3-divinyltetramethyldisiloxane and 1,3,5,7-tetravinyltetramethylcyclotetrasiloxane.

The (aryl+alkenyl)-containing siloxane comprising component (B) is the crucial component for increasing the stability of the platinum complex comprising component (A). In order to increase the stability of the platinum catalyst, this siloxane must contain no more than 8 silicon atoms in each molecule and must contain in each molecule at least one bond as represented by the next formula.

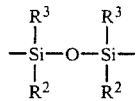

In the preceding formula $R^3$ is an aryl group such as phenyl, etc., and $R^2$ is an alkenyl group such as vinyl, allyl, etc. Such (aryl+alkenyl)-containing siloxanes are exemplified by 1,3-divinyl-1,3-diphenyldimethyldisiloxane and 1,3-divinyltetraphenyldisiloxane.

Component (B) must be added in a quantity of at least 2 moles per 1 mole platinum atoms in component (A), and a stabilizing effect on the platinum catalyst comprising component (A) cannot be obtained at less than 2 moles.

The platinum catalyst composition of the present invention may be prepared by the method of this invention which comprises mixing the aforesaid components (A) and (B), in the amounts stated, and, optionally, then removing a portion of the (alky+alkenyl)-containing siloxane in component (A) by distillation in vacuo.

While the platinum catalyst composition of the present invention may be prepared according to either of these methods, preparation according to the latter method is preferred because it affords a more storage-stable platinum catalyst composition.

Thus, according to the latter method, a platinum catalyst composition with an even more superior storage stability is prepared by removal of part of the platinum-coordinated (alkyl+alkenyl)-containing organosiloxane and part or all of the non-platinum-coordinated (alkyl+alkenyl)-containing organosiloxane in component (A) and substitution with the (phenyl+alkenyl)-containing organosiloxane of component (B).

The platinum catalyst composition of the present invention has the same catalytic activity as prior platinum/siloxane complexes. However, the platinum catalyst composition of the present invention is distinguished by a better high-temperature stability and a better stability against other substances present in the system than the platinum/siloxane complexes known from the art.

Exploiting these distinguishing features, it can be used as a hydrosilylation reaction catalyst in the synthesis of silanes and siloxanes and also as a curing catalyst for those well-known organopolysiloxane compositions which cure by the hydrosilylation reaction.

Thus, the present invention further comprises a curable organopolysiloxane composition comprising the admixture of the platinum catalyst composition of this invention, at 0.1 to 100 parts by weight of platinum atoms, with a million parts by weight of a mixture of an organopolysiloxane having at least 2 alkenyl groups in each molecule and organohydrogenpolysiloxane having at least 2 silicon-bonded hydrogen atoms in each molecule.

The organopolysiloxane having at least 2 alkenyl groups in each molecule and the organohydrogenpolysiloxane having at least 2 silicon-bonded hydrogen atoms in each molecule can be any that are well-known in the organosilicon art.

The present invention is explained below by illustrative examples, in which parts is weight parts in all cases and the % platinum content refers to a weight %.

EXAMPLE 1

200 Grams chloroplatinic acid (platinum content=40%), 400 g 1,3-divinyltetramethyldisiloxane, 400 g sodium bicarbonate, and 1,000 g isopropyl alcohol were mixed and reacted with heating at 70 to 80 degrees Centigrade for 30 minutes. After removal of the produced salt by filtration, the isopropyl alcohol was removed in vacuo at 50 degrees Centigrade, and, after cooling, the precipitated salt was filtered off a second time. This afforded platinum catalyst composition A comprising 1,3-divinyltetramethyldisiloxane and a platinum complex having 1,3-divinyltetramethyldisiloxane as ligand. Its platinum content was 5.4%, and the platinum yield was 97.5%.

36 Grams 1,3-divinyl-1,3-diphenyldimethyldisiloxane was added and mixed into 100 g platinum catalyst composition A, and platinum catalyst composition B was then obtained by conducting distillation in vacuo at 0.03 torr and 50 degrees Centigrade to remove the 1,3-divinyltetramethyldisiloxane. Its platinum content was 8.8%, and the platinum yield from platinum catalyst composition A was 99.2%. These platinum catalyst compositions were analyzed by nuclear magnetic resonance spectral analysis (NMR). Only a single peak at 6133 ppm was observed from platinum catalyst composition A by $^{195}$Pt-NMR. On the other hand, in addition to the peak at 6133 ppm observed for platinum catalyst composition A, platinum catalyst composition B gave a multiplet peak extending over -6080 to -6128 ppm, and the molar ratio between the two was 19%/81%. These results indicated that over 80% of the platinum in platinum catalyst composition B had been converted into a new complex from the platinum complex in platinum catalyst composition A.

Platinum catalyst compositions A and B obtained as above were both diluted to a 2% platinum content by vinyl-terminated polydimethylsiloxane, and the decomposition temperature of the catalyst (temperature at which the transparent solution converted to brown) was measured at a temperature-rise rate of 1 degree Centigrade/minute.

Platinum catalyst composition A and platinum catalyst composition B were also respectively added at 1 ppm (platinum weight) to equimolar pentamethyldisiloxane and 3-vinylheptamethyltrisiloxane. The reaction rates at 25 degrees Centigrade of the obtained siloxane compositions were measured by means of gas chromatography, and these results are reported in Table 1.

As these results make clear, platinum catalyst composition B, which was prepared in accordance with the present invention, was more stable than platinum catalyst composition A while at the same time its catalytic activity remained unchanged.

TABLE 1

|  | present invention platinum catalyst composition B | comparison example platinum catalyst composition A |
|---|---|---|
| decomposition temperature | 138° C. | 85° C. |
| catalytic activity (half-life) | 25 minutes | 25 minutes |

COMPARATIVE EXAMPLE 1

Proceeding as for the synthesis of platinum catalyst composition A in Example 1, a platinum complex was prepared as in Example 1, but using 400 g 1,3-divinyltetramethyldisiloxane and 100 g 1,3-divinyl-1,3-diphenyldimethyldisiloxane in place of the 400 g 1,3-divinyltetramethyldisiloxane. However, the reaction rate was very slow, and platinum complex was not obtained by reaction for 30 minutes at 70 to 80 degrees Centigrade. The platinum yield did not exceed a maximum of 56% during reaction with heating for 60 minutes. When the heated reaction was conducted for longer periods of time, the platinum yield after final filtration fell off due to an increase in platinum black production, and it declined to 35% after 120 minutes.

Moreover, when a platinum catalyst composition was prepared as in Example 1 by replacing the 1,3-divinyltetramethyldisiloxane in Example 1 with 1,3-divinyl1,3-diphenyldimethyldisiloxane, the reaction rate was even slower and the maximum platinum yield was also reduced.

The preceding makes clear that the platinum yield is sharply reduced when a (phenyl+vinyl)-containing organosiloxane is simultaneously present in the synthesis of the alkenyl/Pt complex.

EXAMPLE 2

Platinum catalyst composition B as obtained in Example 1 was mixed to give 5 ppm as the weight of platinum into 100 parts vinyl-terminated dimethylpolysiloxane (viscosity=12,000 centistokes) to prepare a mixture. Curable organopolysiloxane compositions were obtained by the addition to such a mixture, either immediately after mixing or after its ageing for 2 weeks at 70 degrees Centigrade, of 0.9 parts methylhydrogenpolysiloxane with the average structural formula $$Me_3SiO(Me_2SiO)_3(MeHSiO)_5SiMe_3$$

and 0.02 parts methylbutynol. The curing performance was then measured as the gelation time at 130 degrees Centigrade, and these measurement results are reported in Table 2. For comparison, curable organopolysiloxane compositions were prepared as above, but using platinum catalyst composition A in place of platinum catalyst composition B. The curing performance of these compositions was also measured as above, and these results again are reported in Table 2.

These measurement results make it clear that the platinum catalyst composition of the present invention has a high storage stability.

TABLE 2

|  | present invention | comparison example |
|---|---|---|
| immediately after mixing | 30 seconds | 29 seconds |
| after ageing | 29 seconds | 97 seconds |

EXAMPLE 3

A platinum catalyst composition C was prepared by the addition with mixing to homogeneity of 3.0 g 1,3-divinyl-1,3-diphenyldimethyldisiloxane to 10 g platinum catalyst composition A as prepared in Example 1.

Using this platinum catalyst composition C in place of the platinum catalyst composition B used in Example 2, a curable organopolysiloxane composition was then prepared proceeding otherwise the same as in Example 2.

The curing performance of this composition was measured as in Example 2: the gelation time at 130 degrees Centigrade was 33 seconds for the curable organopolysiloxane composition which used the platinum catalyst composition immediately after mixing, while the gelation time at 130 degrees Centigrade was 31 seconds for the curable organopolysiloxane composition which used the aged platinum catalyst composition.

EFFECTS OF THE INVENTION

As discussed above, because the platinum catalyst composition of the present invention consists of component (A) and component (B), it is distinguished by an excellent storage stability. Moreover, the preparative method of the present invention is distinguished by the inexpensive and highly productive preparation of the platinum catalyst composition under consideration.

Furthermore, the curable organopolysiloxane composition which contains said platinum catalyst composition is itself distinguished by an excellent storage stability.

That which is claimed is:

1. A platinum catalyst composition comprising
   (A) a platinum complex having as a ligand an organosiloxane which has no more than 8 silicon atoms in each molecule and contains alkyl and alkenyl groups and which has in each molecule at least one bond as represented by the formula

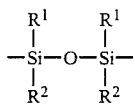

wherein R¹ is an alkyl group having no more than 6 carbon atoms and R² is an alkenyl group, or a mixture of said platinum complex and said organosiloxane; and (B) an organosiloxane which contains aryl and alkenyl groups and has no more than 8 silicon atoms in each molecule and which contains in each molecule at least one bond as represented by the formula

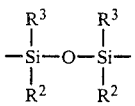

wherein R³ is an aryl group and R² is defined as above, in a quantity of at least 2 moles of component (B) per 1 mole platinum atoms in component (A).

2. A platinum catalyst in accordance with claim 1 in which the organopolysiloxane of component (A) is 1,3-divinyltetramethyldisiloxane and component (B) is 1,3-divinyl-1,3-diphenyldimethyldisiloxane.

3. A platinum catalyst in accordance with claim 1 further comprising a platinum complex having as a ligand an organosiloxane which has no more than 8 silicon atoms in each molecule and contains aryl and alkenyl groups and which contains in each molecule at least one bond as represented by the formula

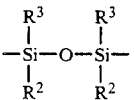

wherein R³ is an aryl group and R² is an alkenyl group.

4. A platinum catalyst in accordance with claim 3 in which the organopolysiloxane of component (A) is 1,3-divinyltetramethyldisiloxane and the organosiloxane ligand which has no more than 8 silicon atoms in each molecule and contains aryl and alkenyl groups and which contains in each molecule at least one bond as represented by the formula

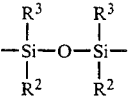

wherein R³ is an aryl group and R² is an alkenyl group is 1,3-divinyl-1,3-diphenyldimethyldisiloxane.

5. A platinum catalyst in accordance with claim 4 which is free of uncomplexed divinyltetramethyldisiloxane.

6. A method for the preparation of a platinum catalyst composition, said method comprising mixing (A) a platinum complex having as a ligand an organosiloxane which has no more than 8 silicon atoms in each molecule and contains alkyl and alkenyl groups and which has in each molecule at least one bond as represented by the formula

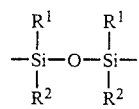

wherein R¹ is an alkyl group having no more than 6 carbon atoms and R² is an alkenyl group, or a mixture of said platinum complex and said organosiloxane; and (B) an organosiloxane which contains aryl and alkenyl groups and has no more than 8 silicon atoms in each molecule and which contains in each molecule at least one bond as represented by the formula

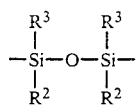

wherein R³ is an aryl group and R² is defined as above, in a quantity of at least 2 moles of component (B) per 1 mole platinum atoms in component (A).

7. A method in accordance with claim 6 in which the organopolysiloxane of component (A) is 1,3-divinyltetramethyldisiloxane and component (B) is 1,3-divinyl-1,3-diphenyldimethyldisiloxane.

8. A method in accordance with claim 6 further comprising removing at least a portion of the organosiloxane in component (A) by distillation in vacuo.

9. A method in accordance with claim 8 in which the organopolysiloxane of component (A) is 1,3-divinyltetramethyldisiloxane and component (B) is 1,3-divinyl-1,3-diphenyldimethyldisiloxane.

10. A method in accordance with claim 9 wherein at least a portion of the complexed divinyltetramethyldisiloxane is removed.

11. The platinum catalyst composition obtained by the method of claim 6.

12. The platinum catalyst composition obtained by the method of claim 7.

13. The platinum catalyst composition obtained by the method of claim 8.

14. The platinum catalyst composition obtained by the method of claim 9.

15. The platinum catalyst composition obtained by the method of claim 10.

* * * * *